US009560965B2

(12) United States Patent
Schuhrke et al.

(10) Patent No.: US 9,560,965 B2
(45) Date of Patent: Feb. 7, 2017

(54) METHOD FOR DETERMINING THE AZIMUTHAL ORIENTATION OF A PATIENT EYE AND EYE SURGICAL APPARATUS THEREFOR

(71) Applicant: Carl Zeiss Meditec AG, Jena (DE)

(72) Inventors: Thomas Schuhrke, Munich (DE); Guenter Meckes, Munich (DE); Lena Henze, Norderstedt (DE); Rolf Werner, Baldham (DE); Christine Kochwagner, Rott am Inn (DE)

(73) Assignee: Carl Zeiss Meditec AG, Jena (DE)

( * ) Notice: Subject to any disclaimer, the term of this patent is extended or adjusted under 35 U.S.C. 154(b) by 102 days.

(21) Appl. No.: 14/192,265

(22) Filed: Feb. 27, 2014

(65) Prior Publication Data

US 2014/0180162 A1    Jun. 26, 2014

Related U.S. Application Data

(63) Continuation-in-part of application No. PCT/EP2012/066211, filed on Aug. 20, 2012.
(Continued)

(30) Foreign Application Priority Data

Sep. 16, 2011    (DE) .................. 10 2011 082 901

(51) Int. Cl.
*A61B 13/00* (2006.01)
*A61B 3/15* (2006.01)
(Continued)

(52) U.S. Cl.
CPC ............. *A61B 3/152* (2013.01); *A61B 3/0025* (2013.01); *A61B 3/0033* (2013.01);
(Continued)

(58) Field of Classification Search
CPC ............ A61B 5/16; A61B 3/113; A61B 5/162
(Continued)

(56) References Cited

U.S. PATENT DOCUMENTS 5,865,832 A    2/1999    Knopp et al.
6,254,046 B1    7/2001    Biber
(Continued)

FOREIGN PATENT DOCUMENTS

DE             36 07 721 A1    9/1987
DE    10 2009 030 504 A1    12/2010
(Continued)

OTHER PUBLICATIONS

Machine English Translation of DE 10 2009 030504 A1.*
(Continued)

*Primary Examiner* — Daniel Cerioni
(74) *Attorney, Agent, or Firm* — Walter Ottesen, P.A.

(57) ABSTRACT

An eye surgery apparatus has imaging optics for generating an observation image of a patient eye. A device determines the azimuthal orientation of the patient eye with respect to a reference which is fixed with respect to the patient eye. The device includes a display unit for simultaneously displaying a section of an observation image of the eye and a reference image thereof. An input interface permits an observer to move the displayed section of the observation image relative to the displayed section of the reference image. A measuring system determines the azimuthal orientation of the observation image and reference image. A computer program calculates the center of the limbus of the observation image and reference image. The display unit displays the pixels of the observation image of the patient eye with polar coordinates. The pixels of the reference image of the patient eye are displayed with polar coordinates.

9 Claims, 4 Drawing Sheets

Related U.S. Application Data (60) Provisional application No. 61/535,769, filed on Sep. 16, 2011.

(51) Int. Cl.
    *A61B 3/00*     (2006.01)
    *A61B 3/113*     (2006.01)
    *A61B 3/117*     (2006.01)
    *G06T 7/00*     (2006.01)

(52) U.S. Cl.
    CPC ............ *A61B 3/0058* (2013.01); *A61B 3/113* (2013.01); *A61B 3/1173* (2013.01); *A61B 3/15* (2013.01); *G06T 7/0044* (2013.01); *G06T 2207/30041* (2013.01)

(58) Field of Classification Search
    USPC ........................................................ 600/558
    See application file for complete search history.

(56) References Cited

U.S. PATENT DOCUMENTS

| | | |
|---|---|---|
| 6,866,661 B2 | 3/2005 | Gray et al. |
| 2004/0143245 A1 | 7/2004 | Gray et al. |
| 2005/0119642 A1 | 6/2005 | Grecu et al. |
| 2005/0270486 A1 | 12/2005 | Teiwes et al. |
| 2014/0111630 A1* | 4/2014 | Pires ...................... A61B 3/113 348/78 |

FOREIGN PATENT DOCUMENTS

| | | | |
|---|---|---|---|
| DE | 102009030504 A1 * | 12/2010 | ............ A61B 3/113 |
| DE | 10 2009 052 128 A1 | 4/2011 | |
| WO | WO 2009/080790 A1 | 7/2009 | |
| WO | WO 2009/080791 A1 | 7/2009 | |

OTHER PUBLICATIONS

International Preliminary Report on Patentability of the international searching authority dated Mar. 27, 2014 in international patent application PCT/EP2012/066211 on which the claim of priority is based.

Written Opinion of the international searching authority dated Nov. 22, 2012 in international patent application PCT/EP2012/066211 on which the claim of priority is based.

International Search Report of the international searching authority dated Nov. 22, 2012 in international patent application PCT/EP2011/066211 on which the claim of priority is based.

\* cited by examiner

METHOD FOR DETERMINING THE AZIMUTHAL ORIENTATION OF A PATIENT EYE AND EYE SURGICAL APPARATUS THEREFOR

CROSS REFERENCE TO RELATED APPLICATIONS

This application is a continuation-in-part application of international patent application PCT/EP2012/066211, filed Aug. 20, 2012, which designates the United States and claims priority from U.S. Provisional Application No. 61/535,769, filed Sep. 16, 2011, and German patent application 10 2011 082 901.6, filed Sep. 16, 2011. The present continuation application claims priority to each of the above applications and incorporates herein the entire contents thereof by reference.

FIELD OF THE INVENTION

The invention relates to an eye surgery apparatus having imaging optics for generating an observation image of a patient's eye and having a device for determining the azimuthal orientation of a patient's eye with respect to a reference which is fixed with respect to the patient's eye. In addition, the invention relates to a method and a computer program which can be used to determine the azimuthal orientation of a patient's eye with respect to a reference which is fixed with respect to the patient's eye, for example in cataract surgery.

BACKGROUND OF THE INVENTION

During the cataract operation, the body's own natural lens of a patient's eye, in which a cataract has developed, is replaced with an artificial lens, a so-called intraocular lens. An opening into the capsular bag is prepared within the inner edge of the iris by means of an incision through the sclera or cornea. The natural lens is then shattered with an ultrasonic instrument through this opening and is then removed. After the natural lens has been removed, the intraocular lens is introduced through the opening in the capsular bag of the patient's eye.

Intraocular lenses with a spherical, aspherical, multifocal and also a toric geometry are used, in particular, in eye surgery. In the case of toric intraocular lenses, it is necessary, in order to compensate for patients' visual defects, for the axis of the torus of the intraocular lens to be oriented in a defined manner in the patient's eye during the cataract operation.

During the cataract operation, the surgeon is faced with the problem that the patient's eye can move during an operation even with local anesthesia. The image of the object area that is presented to a surgeon during a cataract operation is therefore not stationary.

Therefore, in order to indicate the azimuthal orientation of the patient's eye to a surgeon in an operation, the patient's eye is often provided with a mark, which indicates a direction, before the operation.

DE 10 2009 030 504 A1 describes an eye surgery microscopy system of the type mentioned at the outset, in which the azimuthal orientation of a patient's eye provided with a mark can be automatically detected. This eye surgery microscopy system has imaging optics for generating the image of an object plane. It contains an electronic image sensor which receives the image of the object plane. The eye surgery microscopy system has a computer unit which is connected to the image sensor. The computer unit can be used to calculate the position of the center of the limbus or of the iris of a patient's eye. For this purpose, the computer unit contains a computer program which determines the azimuthal orientation of a patient's eye provided with a mark by means of correlation with a reference image.

DE 10 2009 052 128 A1 discloses an eye surgery microscopy system containing a measuring device which can be used to determine an axis of the astigmatism of a patient's eye in an ophthalmological operation. In this eye surgery microscopy system, a determined axis of the astigmatism can be displayed in a manner superimposed on the observation image of the patient's eye.

U.S. Pat. No. 5,865,832 discloses an eye surgery microscopy system containing imaging optics which are automatically corrected when a patient's eye moves. For this purpose, the imaging optics are connected to a device for detecting the position of the patient's eye. This device contains an image sensor which is used to continuously capture the patient's eye in order to correct the imaging optics on the basis of a change in the image captured with the image sensor.

U.S. Pat. No. 6,866,661 B2 describes a device for calculating the change in orientation of a patient's eye in an eye surgery system for laser in-situ keratomileusis. In this device, the patient's eye is continuously captured with an image sensor. The continuously captured images are subjected to image evaluation therein. During this image evaluation, characteristic structures of the patient's eye, for example blood vessels of the sclera, are then determined in order to calculate the change in the orientation of the patient's eye from the locations of these structures in the continuously captured images.

United States patent application publication 2005/0270486 discloses an eye tracking system and a method for determining a position of an eye or a part of an eye in an image of an image sequence by performing a comparison between said image and a reference image. This method includes aligning a set of images and computing an enhanced reference image based on a combination of the set of aligned images. The position in said image of the image sequence is determined by comparing the image of the image sequence to the enhanced reference image to yield a motion estimation between the reference image and the image of the image sequence.

SUMMARY OF THE INVENTION

An object of the invention is to provide an eye surgery apparatus and a method for determining the azimuthal orientation of a patient's eye, which can be used to reliably determine the azimuthal orientation of a patient's eye without the patient's eye necessarily being marked.

This object is achieved with an eye surgery apparatus having a device including a visual display unit for simultaneously displaying a section of an observation image of the patient's eye, which is captured by the imaging optics and contains at least one segment of the sclera, the section being composed of pixels, and a reference image of the patient's eye, which is composed of pixels and contains this segment of the sclera, and has an input interface which makes it possible for an observer to move the displayed section of the captured observation image of the patient's eye relative to the displayed section of the reference image, and contains a measuring system which can be used to determine an azimuthal orientation of the observation image and of the reference image, which orientation is changed during the relative movement.

The invention uses the fact that the azimuthal orientation of a patient's eye, that is, the azimuth angle or angle of rotation of the patient's eye, can be determined in a polar coordinate system, which is fixed with respect to the patient's eye and the origin of which is at the center of the limbus and in which the patient's eye can rotate about a perpendicular axis through the origin of the polar coordinate system, using structures in the sclera around the edge of the limbus of the patient's eye or the iris by comparing image information. The sclera extends in that region of the eye which adjoins the outer edge of the iris, that is, in that region which adjoins the limbus.

One idea of the invention is, in particular, for a surgeon, to whom the pixels of the image of the patient's eye, as captured by the imaging optics of the eye surgery apparatus, are displayed with the pixels of a reference image of the patient's eye in the polar coordinates of a polar coordinate system, the center of which coincides with a calculated center of the limbus and/or of the iris of the patient's eye, to be able to identify in a particularly effective manner, in the patient's eye, those structures which are suitable for determining the azimuthal orientation of the patient's eye with respect to a reference which is fixed with respect to the patient's eye and is in the form of a reference image.

The inventors have namely realized that the practice of determining the azimuth angle or angle of rotation of a patient's eye in a cataract operation using two images which cannot be moved, are displayed beside one another and/or alternately in terms of time and are not subjected to any suitable coordinate transformation is very inaccurate and unreliable. The inventors have also realized that the practice of determining the azimuth angle or angle of rotation of a patient's eye by superposing an observation image of the patient's eye on a reference image likewise does not make it possible to reliably determine an astigmatism axis.

In order to calculate the center of the limbus and/or of the iris of the image of the patient's eye, as captured by the imaging optics, and of the reference image, the device contains a computer unit having a computer program. This computer program can calculate the center of the limbus and/or of the iris of the observation image of the patient's eye, as captured by the imaging optics, and of the reference image. In this case, the visual display device preferably displays the pixels of the observation image of the patient's eye, as captured by the imaging optics, with polar coordinates in a polar coordinate system, the center of which coincides with the calculated center of the circular structure of the limbus and/or of the iris of the patient's eye. The pixels of the reference image of the patient's eye are likewise preferably also displayed with polar coordinates in a polar coordinate system, the center of which corresponds to the calculated center of the circular structure of the limbus and/or of the iris of the patient's eye on which the reference image is based.

By virtue of the fact that the visual display device displays the pixels of the observation image of the patient's eye, as captured by the imaging optics, and displays the pixels of the reference image of the patient's eye in an image strip, an observer can compare mutually corresponding structures of the observation image and of the reference image in a particularly effective manner. For this purpose, it is advantageous if the image strip containing the pixels of the observation image of the patient's eye, as captured by the imaging optics, and the image strip containing the pixels of the reference image of the patient's eye adjoin one another.

It is favorable if the image strip containing the pixels of the observation image of the patient's eye, as captured by the imaging optics, is parallel to the image strip containing the pixels of the reference image of the patient's eye.

One idea of the invention is also that the azimuthal orientation of the observation image of the patient's eye relative to the reference image can be determined in a particularly exact manner by virtue of the fact that the pixels in the image strip containing the pixels of the observation image of the patient's eye, as captured by the imaging optics, can be shifted in the longitudinal direction of the image strip on the basis of a shift signal specified at an input interface, and/or by virtue of the fact that the pixels in the image strip containing the pixels of the reference image of the patient's eye can be shifted on the basis of a shift signal specified at the input interface.

The input interface may be in the form of a touch-sensitive user interface of the visual display device. It is advantageous if the device for determining the azimuthal orientation of the patient's eye has a display unit on which the change in the azimuthal orientation of the image and of the reference image, as determined using the measuring system, is indicated.

By virtue of the fact that the device has a computer unit having a computer program for calculating a direction of the astigmatism of the patient's eye, based on the observation image, from the change in the azimuthal orientation of the observation image relative to the reference image, as determined using the measuring system, and a direction of the astigmatism of the patient's eye, which direction is stored in a data memory of the computer unit and is based on a reference, for example the reference image, it is possible to display the direction of the astigmatism in the observation image to an observer. In this case, it is advantageous if the computer unit generates an item of display information, which is superimposed on the image of the patient's eye, in order to display the direction of the astigmatism of the patient's eye, which direction is based on the observation image. This display information may be an astigmatism axis, for example. In addition, it is advantageous if the imaging optics are arranged in an operating microscope which has a binocular viewer and has a device for reflecting in data, which device has a display which is connected to the computer unit and is intended to display the display information in the object plane in a manner superimposed on the operating area.

One idea of the invention is to determine the azimuthal orientation of a patient's eye with respect to a reference which is fixed with respect to the patient's eye by comparing at least one section of an observation image of the patient's eye, which comprises a segment of the limbus and/or of the iris, with a section of a reference image of the patient's eye containing this segment. The azimuthal orientation of the patient's eye relative to the azimuthal orientation of the patient's eye, on which the reference image is based, can then be namely inferred from the azimuthal offset ($\Delta\phi$) of characteristic, mutually corresponding structures of the observation image of the patient's eye and of the reference image in the region of the limbus. In order to compare the observation image of the patient's eye with the reference image, the section of the observation image and the section of the reference image of the patient's eye are displayed to an observer in such a manner that they can be moved relative to one another. That is to say, the observer can move these images relative to one another on a screen display by initiating an image control function. In this case, the change in an azimuthal orientation of the observation image relative to the reference image is determined.

It is advantageous if the center of the limbus and/or of the iris is calculated for the observation image and for the reference image. In particular, it is advantageous if the section of the image of the patient's eye and the section of the reference image are each displayed in polar coordinates in a polar coordinate system, the center of which corresponds to the calculated center of the limbus and/or of the iris in the observation image and in the reference image.

In this case, one idea of the invention is that the section of the observation image is shifted relative to the section of the reference image along an axis corresponding to the azimuth angle ($\phi$) in the polar coordinate systems until mutually corresponding structures of the observation image of the patient's eye and of the reference image are beside one another.

The invention also comprises a computer program for determining the azimuthal orientation of an observation image of a patient's eye with respect to a reference which is fixed with respect to the patient's eye, which computer program calculates the center of the limbus and/or of the iris for an observation image and a reference image of a patient's eye and determines the change in the azimuthal orientation ($\Delta\phi$) of the observation image relative to the reference image from a movement of a section of the observation image, which section contains at least one segment of the limbus and/or of the iris, relative to the reference image of the patient's eye, which movement can be input via an input interface.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
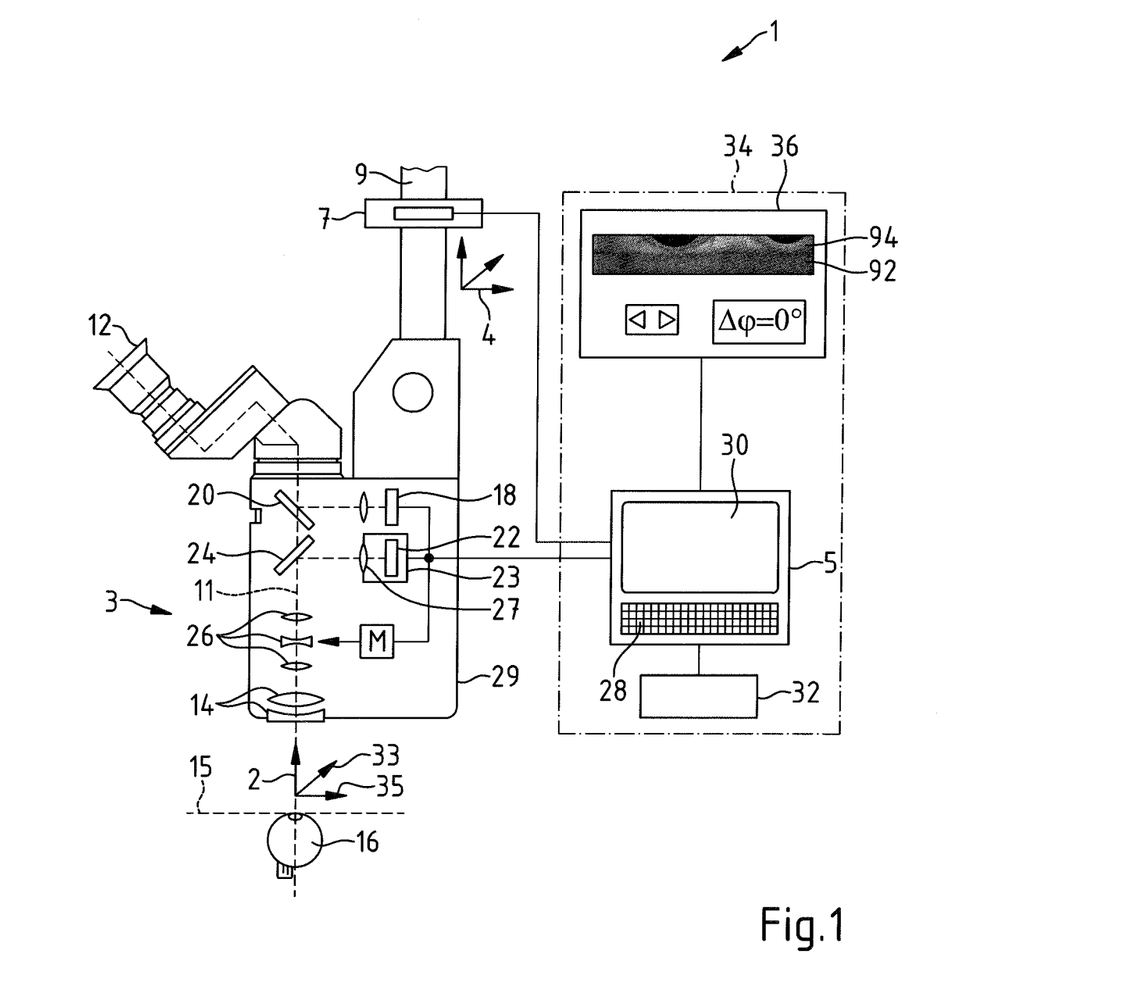
FIG. 1 shows an eye surgery apparatus having a computer unit, a video camera and a touch-sensitive screen.

The eye surgery apparatus 1 in FIG. 1 comprises an operating microscope 3 having a computer unit 5. The operating microscope 3 has an operating microscope base body 29. It is accommodated on the arm 9 of a stand with an XY adjusting device 7. A suitable XY adjusting device is described, for example, in U.S. Pat. No. 6,254,046. The operating microscope 3 makes it possible for an observer to view a patient's eye 16 with variable magnification with a binocular observation beam path 11 through a binocular viewer 12, a magnification system 26 and a microscope main lens 14 in an object plane 15. The operating microscope 3 has a device for reflecting in data, which device has a display 18 and a beam splitter 20. A video camera 23 containing a CCD module as an image sensor 22 is also integrated into the operating microscope 3. The object image is supplied to the image sensor 22 via a beam splitter 24 in the observation beam path 11 and via an imaging lens 27. In this case, the microscope main lens 14 and the magnification system 26 as well as the imaging lens 27 act as imaging optics for the image sensor 22. The video camera 23 is a PAL color camera, for example. It provides RGB image information with a red color channel (R), a green color channel (G) and a blue color channel (B). The video camera 23 can be used to continuously capture observation images of the patient's eye 16 in real time.

The eye surgery apparatus 1 contains a visual display device 34 having a computer unit 5. The computer unit 5 can be used to control the operating microscope 3. The computer unit 5 acquires image data recorded using the image sensor 22 of the video camera 23 in order to process the data further using a computer program. The computer unit 5 has an input interface 28 in the form of a keyboard. The computer unit 5 comprises a screen 30 which is used as an output interface. A data memory 32 is assigned to the computer unit 5. The data memory 32 contains a preoperatively captured image of the patient's eye 16. The astigmatism axis preoperatively recorded using a known diagnostic device (not illustrated any further) is stored for the preoperatively captured image of the patient's eye 16 in the data memory 32.

The computer unit 5 is connected to a touch-sensitive external screen 36 of the visual display device 34. Image data processed by the computer unit 5 can therefore be displayed both on the external screen 36 and in the device for reflecting in data which has the display 18 in the operating microscope 3.

Figure 2:
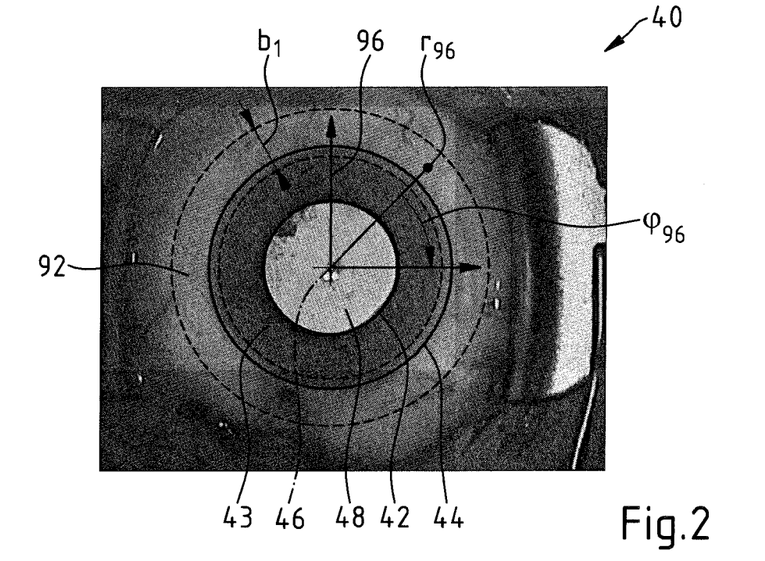
FIG. 2 shows the observation image of a patient's eye captured with the video camera.

FIG. 2 shows the observation image 40 of the patient's eye 16, as captured in the object plane 15 by the imaging optics (14, 26, 27) of the operating microscope 3 in the eye surgery apparatus 1 with the video camera 23. The observation image 40 of the patient's eye 16 has a first circular structure 42 formed by the inner edge of the iris 43. A second circular structure 44 is formed in the patient's eye 16 by the limbus, that is to say the transition between the sclera and the cornea in the patient's eye. The iris 43 and the limbus 44 have a common center 46 which is situated in the region of the lens 48 of the patient's eye 16.

In order to determine the position of the center 46 of the circular structure of the limbus 44 of the patient's eye 16, the computer unit 5 correlates the observation image 40 captured using the image sensor 22 in the object plane 15 with annular comparison objects of different sizes. This is described in detail on page 3, line 12 to page 4, line 14, and page 5, line 9 to page 9, line 15, of international patent application WO2009/080791 (PCT/EP2008/068104) and also in international patent application WO2009/080790 (PCT/EP2008/068103).

Correlation is effected by calculating a correlation function, preferably by varying the location, with the result that the correlation function is a function of the location variables. In this case, the values of the pixels of the observation image are calculated with the values of the pixels of the comparison object while the comparison object is moved over the image. The value of the correlation function is a measure of the correspondence between the observation image and the comparison object. With maximum correspondence between the observation image and the comparison object, that is to say if the characteristic feature of the comparison object and the characteristic feature sought in the image lie on top of one another, the value of the correlation function is at a maximum.

Figure 3:
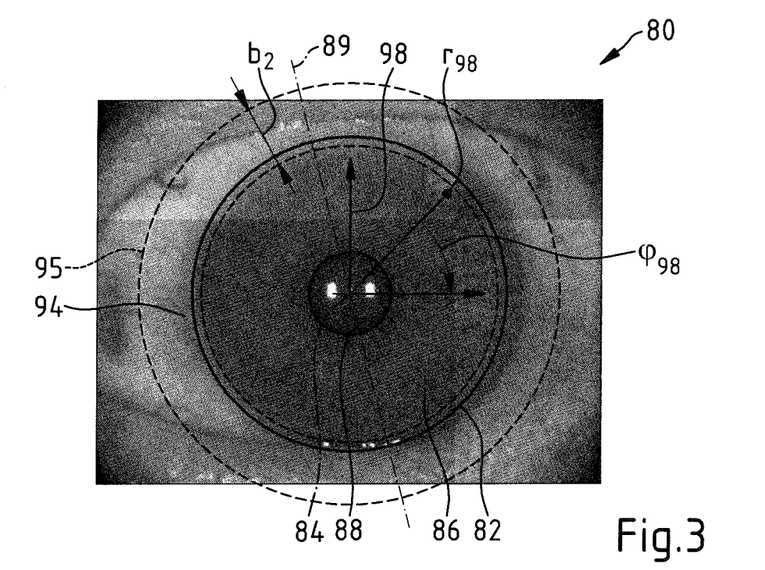
FIG. 3 shows a reference image of the patient's eye, which image is stored in a memory of the computer unit.

FIG. 3 shows the reference image 80 of the patient's eye 16, which is stored in the data memory 32 of the computer unit 5, in the operating microscope 3. Like the operating microscope 3, the reference image 80 is a fixed reference with respect to the observation image 40.

The reference image 80 of the patient's eye 16 likewise shows the circular structure 82 of the limbus with the center 84. The edge of the iris 86, that is, the pupil, has a circular structure 88. However, the iris 86 of the patient's eye 16 is widened to a lesser extent in the reference image 80 than in the observation image 40. The magnification for the reference image 80 and the magnification of the observation image 40 captured in the eye surgery microscopy system 1 from FIG. 1 are generally different.

The patient's eye 16 has the astigmatism axis 89 depicted in the reference image 80. The axis 89 is preoperatively determined for the patient's eye 16 in the above-mentioned diagnostic device. The orientation of the axis 89 of the reference image 80 in a coordinate system which is fixed with respect to the operating microscope 3 was determined in the relevant diagnostic device and is likewise stored in the data memory 32 of the eye surgery apparatus 1. The position of the center 84 of the circular structure 82 of the limbus is determined in the computer unit 5 for the reference image 80, like for the observation image 40 captured using the video camera 23.

The computer unit 5 contains a computer program for calculating coordinate transformations. The computer program transforms an annular image segment 92 with the width (b1), which comprises a section of the circular structure 44 of the limbus in the image 40, and an annular image segment 94 of a part (delimited by the dashed line 95) of the sclera of the patient's eye 16 with the width (b2) around a section of the circular structure 82 of the limbus in the reference image 80 into a polar coordinate representation on the basis of an input at the input interface 28 and displays it on the screen 34. The polar coordinate system (96, 98) on which this polar coordinate representation is based is shown in FIG. 2 and FIG. 3. The origin of the polar coordinate systems (96, 98) is respectively the center (46, 84) of the limbus 44 and 94 in the observation image 40 of the patient's eye and in the reference image 80, as calculated by means of correlation with comparison objects.

Figure 4:
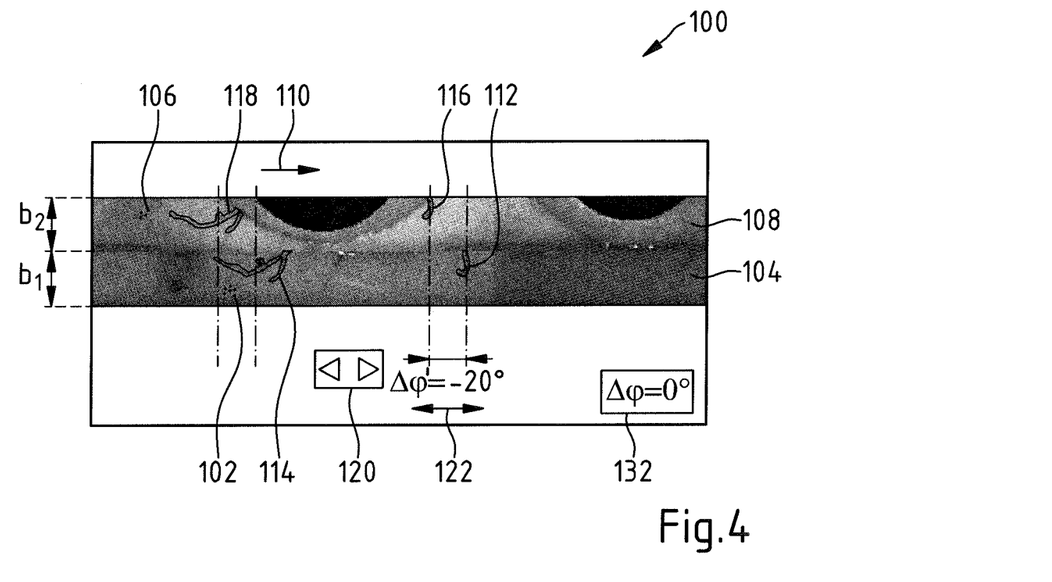
FIG. 4 shows a display on the touch-sensitive screen in order to determine the azimuthal orientation of the patient's eye.

FIG. 4 shows a display 100 on the screen 36. The pixels 102 of the image of the patient's eye 16, as captured by the imaging optics (14, 26, 27) of the eye surgery microscopy system 1, are arranged in the image strip 104. The pixels 102 correspond to the annular image segment 92 of the observation image 40 of the patient's eye 16, as shown in FIG. 2. The pixels 106 of the reference image 80 are situated in the image strip 108. The pixels 106 lie in the image segment 94 of the reference image 80 of the patient's eye 16, as shown in FIG. 3. The pixels (102, 106) in the image strips (104, 108) have an azimuth angle ($\phi$96, $\phi$98) which increases in the direction of the arrow 110. The image strip 104 has structures (112, 114) to which a structure (116, 118) in the image strip 108 respectively corresponds.

The touch-sensitive screen 34 has an interactive user interface with an input window 120. The input window 120 can be used to move the pixels 102 in the image strip 104 to the left or to the right according to the double-headed arrow 122. This movement of the pixels 102 in the image strip 104 corresponds in this case to the rotation of the image 40 of the patient's eye 16, as captured by the imaging optics of the eye surgery microscopy system 1 with the video camera 23, relative to the reference image 80 around the origin 46 of the coordinate system 96.

It is thus possible for an observer to arrange the mutually corresponding structures (112, 114) and (116, 118) in the image strips (104, 108) beside one another. For the display 100, the observer must move the pixels 102 in the image strip 104 to the left by the angle $\Delta\phi' \approx -20°$ in the direction of the double-headed arrow 122 by actuating the control function in the input window 120. In this case, the pixels 102 in the image strip 104 are not moved in the axis perpendicular to the double-headed arrow 122. The pixels 102 in the direction perpendicular to the double-headed arrow 122 are not moved even when the patient's eye 16 moves.

Figure 5:
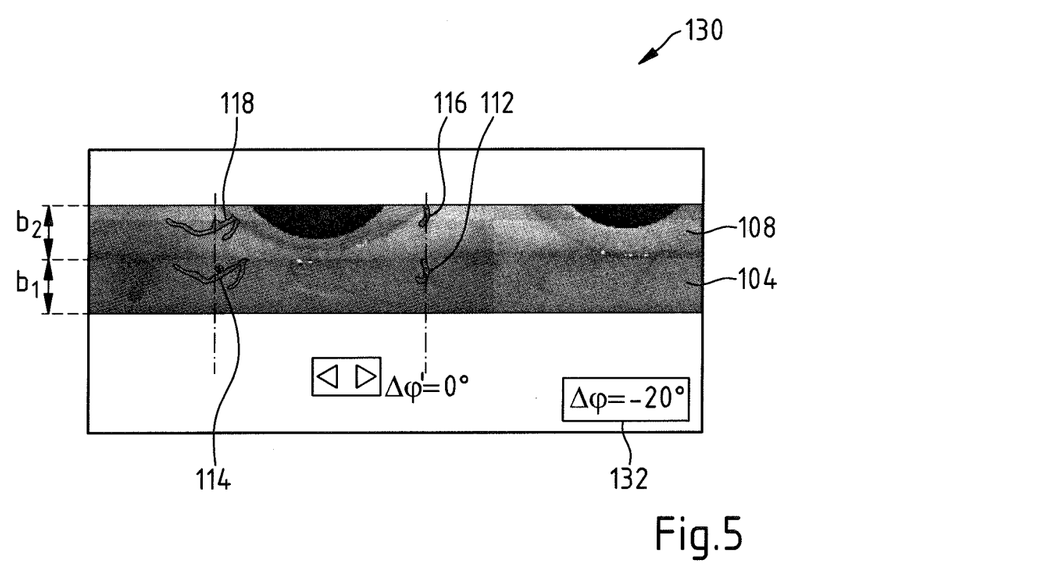
FIG. 5 shows another display on the touch-sensitive screen.

FIG. 5 shows a display 130 on the touch-sensitive screen 34. The computer unit 5 contains a measuring routine for the purpose of measuring the azimuthal shift of the pixels 102 in the image strip 104 relative to the image strip 108. This measuring routine acts as a measuring system. It generates a display window 132 on the touch-sensitive screen 34. The shifting of the pixels 102 is displayed to the observer as an azimuth angle value $\Delta\phi$ in the display window 132.

Figure 6:
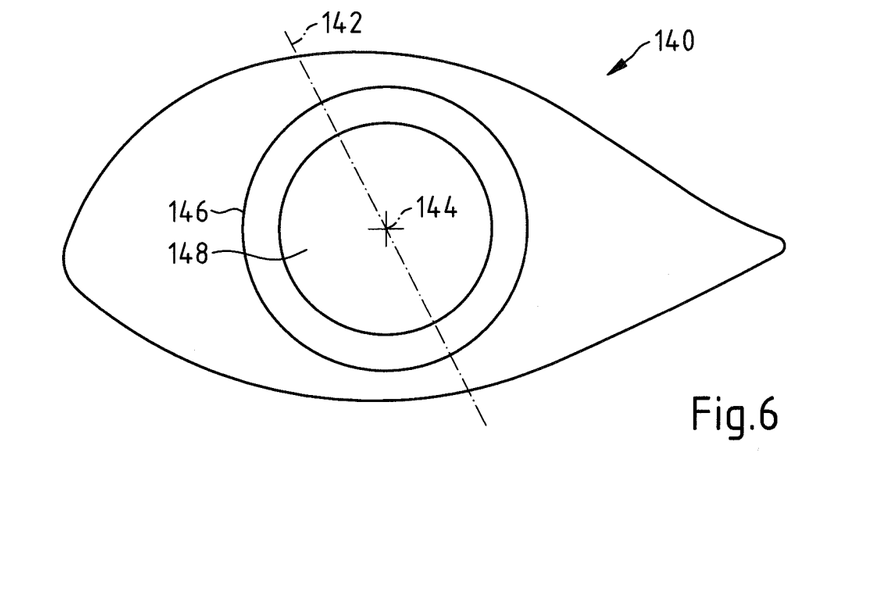
FIG. 6 shows an observation image of the patient's eye in the eye surgery apparatus; and, FIG. 7 shows a toric intraocular lens with position marks.

FIG. 6 shows an observation image 140 of the patient's eye 16 on the binocular viewer 12 of the eye surgery microscopy system 1 in FIG. 1. In this case, an axis 142 through the pupil 148, which is reflected in using the device for reflecting in data in the operating microscope 3, is superimposed on the observation image 140 of the patient's eye 16. The axis 142 runs through the center 144 of the limbus 146 of the patient's eye 16. The axis 142 corresponds to the direction of the astigmatism in the patient's eye 16. The axis 142 is calculated in the computer unit 5, on the basis of an input on the input interface 28, from the astigmatism axis 89 in the reference image 80 from FIG. 3, which is stored in the memory 32, and the shift of the observation image 40 (shown in FIG. 2) of the patient's eye, as measured using the measuring system, with respect to the reference image 80.

Figure 7:
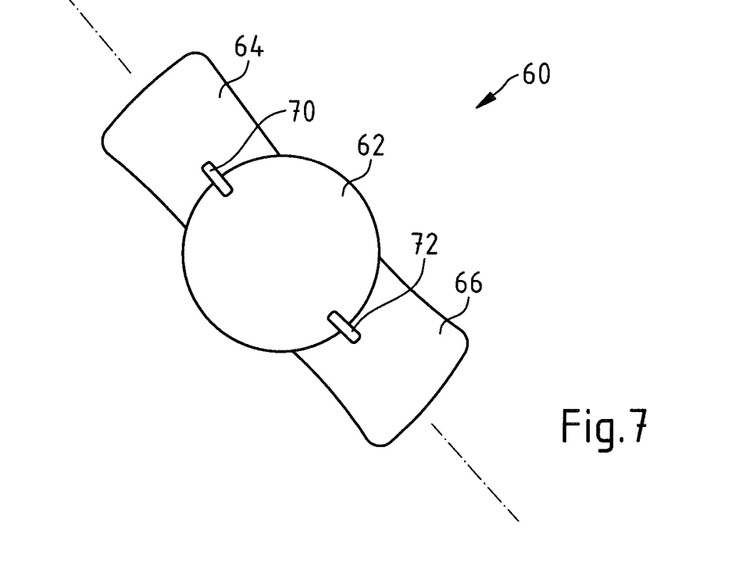

FIG. 7 shows a toric intraocular lens 60. The intraocular lens 60 has a lens body 62 with a toric geometry and comprises holding sections (64, 66) which bear the lens body 62. There are marks (70, 72) on the holding sections (64, 66). These marks (70, 72) project into the lens body 62. The marks (70, 72) make it possible for a surgeon to orient such a lens during the cataract operation to a target axis 142 which is generated on the display 18 in the eye surgery microscopy system 1 from FIG. 1 with the device for reflecting in data and is indicated in FIG. 6.

In summary, the following can be stated in particular: the invention relates to an eye surgery apparatus 1 having imaging optics (14, 26, 27) for generating an observation image 40 of a patient's eye 16. The eye surgery apparatus 1 has a device 36 for determining the azimuthal orientation of a patient's eye 16 with respect to a reference (3, 80) which is fixed with respect to the patient's eye 16. The device 36 contains a visual display device 34 for simultaneously displaying a section 92 of an observation image 40 of the patient's eye 16, which is captured by the imaging optics (14, 26, 27) and contains at least one segment of the limbus 44 or of the iris 43, the section being composed of pixels 102, and a reference image 80 of the patient's eye 16, which is composed of pixels 106 and contains this segment of the limbus 98 or of the iris 86. The device 36 has an input interface 28 which makes it possible for an observer to move the displayed section 92 of the captured observation image 40 of this patient's eye 16 relative to the displayed section 94 of the reference image 80. The device 36 comprises a measuring system which can be used to determine the azimuthal orientation of the observation image 40 and of the reference image 80, which orientation is changed during the relative movement. The device 36 has a computer unit 5 having a computer program for calculating the center 46 of the limbus 44 and/or of the iris 43 of the observation image 40 of the patient's eye 16, as captured by the imaging optics (14, 26, 27), and of the reference image 80. The visual display device 34 displays the pixels 102 of the observation image 40 of the patient's eye 16, as captured by the imaging optics (14, 26, 27), with polar coordinates in a polar coordinate system 96, the center 46 of which coincides with the calculated center of the circular structure 44 of the limbus and/or of the iris 43 of the patient's eye 16. It displays the pixels 106 of the reference image 80 of the patient's eye 16 with polar coordinates in a polar coordinate system 98, the center 84 of which corresponds to the calculated center of the circular structure 94 of the limbus of the patient's eye 16 on which the reference image 80 is based.

It is understood that the foregoing description is that of the preferred embodiments of the invention and that various changes and modifications may be made thereto without departing from the spirit and scope of the invention as defined in the appended claims.

What is claimed is:

1. An eye surgical apparatus comprising:
   imaging optics for generating observation images of a patient eye; and,
   a device for determining and displaying an azimuthal orientation of the patient eye with respect to a reference fixed with respect to the patient eye;
   said device including:
   a visual display unit configured to simultaneously display:
      a section, composed of pixels, of a captured observation image of the patient eye captured by said imaging optics;
      said section containing at least one segment of a sclera and being displayed as a first rectangular image strip representing, in polar coordinates, a first annular image segment of the captured observation image;
      a reference image, composed of pixels, of the patient eye and containing said at least one segment of the sclera being displayed as a second rectangular image strip representing, in said polar coordinates, a second annular image segment of the reference image; and,
      said first and second image strips being displayed mutually parallel to one another in a mutually adjoining manner;
   an input interface configured to permit an observer to effect a linear movement of the first rectangular image strip representing the first annular image segment of the captured observation image of the patient eye relative to the second rectangular image strip representing the second annular image segment of the reference image whereby an azimuthal orientation of said captured observation image relative to said reference image changes during said linear movement;
   a measuring system configured to determine a change of azimuthal orientation of the captured observation image relative to said reference image because of said linear movement;
   a computer unit having a computer program for computing the center of a first circular structure of a limbus and/or of an iris of said captured observation image and for computing the center of a second circular structure of the limbus and/or of the iris of said reference image; and,
   said visual display unit being further configured to display said pixels of said captured observation image with polar coordinates having a center coincident with the computed center of said first circular structure and to display said pixels of said reference image with polar coordinates in a polar coordinate system having a center coincident with the computed center of said second circular structure.

2. The eye surgical apparatus of claim 1, wherein said input interface is a first input interface and said first strip defines a longitudinal axis; said eye surgical apparatus comprises a second input interface configured to provide shift signals; and, wherein said pixels in said first image strip are shiftable along said longitudinal axis in response to a first one of said shift signals specified at said second input interface; and/or, said pixels in said second strip are shiftable in response to a second one of said shift signals specified at said second input interface.

3. The eye surgical apparatus of claim 2, wherein said second input interface is a touch-sensitive user interface of said visual display unit.

4. The eye surgical apparatus of claim 1, wherein said visual display unit is a first visual display unit and said device for determining azimuthal orientation of the patient eye further includes a second display unit for displaying said change in the azimuthal orientation of said captured observation image relative to said reference image as determined with said measuring system.

5. The eye surgical apparatus of claim 4, wherein said computer unit has a computer program for computing a change in an azimuthal orientation of the patient eye based on said change determined with said measuring system and on a direction of the astigmatism of the patient eye stored in a data memory of said computer unit and based on a reference.

6. The eye surgical apparatus of claim 5, wherein said reference is said reference image.

7. The eye surgical apparatus of claim 5, wherein said computer unit is configured to generate an item of display information, which is superposed on said captured observation image of the patient eye, in order to display the direction of the astigmatism of the patient eye on said captured observation image.

8. The eye surgical apparatus of claim 7, wherein said display information is an astigmatism axis.

9. The eye surgical apparatus of claim 7, further comprising a surgical microscope defining an object plane and accommodating said imaging optics; said surgical microscope including: a binocular viewer to facilitate viewing through said imaging optics; and, a reflecting device for reflecting in data; and, said reflecting device including a display connected to said computer unit and said display being configured to display said display information in said binocular viewer in a manner superposed on an operating area in said object plane.

* * * * *